US00PP33437P2

(12) United States Plant Patent
Korlipara

(10) Patent No.: US PP33,437 P2
(45) Date of Patent: Aug. 31, 2021

(54) ***ECHINACEA* PLANT NAMED 'TNECHSDR'**

(50) Latin Name: ***Echinacea* spp.**
Varietal Denomination: TNECHSDR

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/165,066

(22) Filed: Feb. 2, 2021

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS https://www.floraldaily.com/article/9207388/terra-nova-nurseries-reveals-new-varieties-digital-content/; Apr. 9, 2020; 10 pages.*

* cited by examiner

*Primary Examiner* — Kent L Bell
(74) *Attorney, Agent, or Firm* — Klarquist Sparkman, LLP

(57) ABSTRACT

A new and distinct *Echinacea* plant named 'TNECHSDR' characterized by ruby-colored ray florets, enlarged ruby-colored disc florets forming an anemone-type inflorescence, a multicrown, medium habit with upright strong stems, and excellent vigor.

1 Drawing Sheet

Botanical denomination: *Echinacea* spp.
Variety designation: 'TNECHSDR'.
Trademark designation: Sunny Days Ruby™.

BACKGROUND OF THE INVENTION

The present invention relates to a new and distinct cultivar of *Echinacea* and given the cultivar name 'TNECHSDR'. *Echinacea* is in the family Asteraceae. The new cultivar is part of a planned breeding program for a landscape series with compact habits and profuse inflorescences. The exact parents of this selection are unknown, unnamed, proprietary interspecific hybrids bred from *Echinacea paradoxa, Echinacea purpurea*, and *Echinacea tennesseensis*.

Compared to *Echinacea* 'TNECHCMR' (U.S. Plant Pat. No. 28,749), the new cultivar is slightly taller, more upright, with inflorescences that are bright ruby-colored rather than raspberry-red.

Compared to *Echinacea* 'Balsceras' (Double Scoop Raspberry), U.S. Plant Pat. No. 23,117, this new cultivar is much shorter, forms more crowns from the base, and has larger inflorescences that are a brighter ruby color.

This new *Echinacea* cultivar is uniquely distinguished by:

1. ruby-colored ray florets,
2. enlarged ruby-colored disc florets forming a large anemone-type inflorescence,
3. a multicrown, strong, upright habit, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding asexually propagations. The present invention has not been evaluated under all possible environmental conditions. The phenotype may vary with variations in environment without a change in the genotype of the plant.

BRIEF DESCRIPTION OF THE DRAWING

FIG. 1 shows an eighteen-month-old *Echinacea* 'TNECHSDR' growing in the trial field in full sun in late July in Canby, Oreg.

DETAILED PLANT DESCRIPTION

The following is a detailed description of the new *Echinacea* cultivar based on observations of 18-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition.

Plant:

*Type*.—Herbaceous perennial.
*Hardiness*.—USDA Zones 4 to 9.
*Size*.—Grows to 80 cm wide and 51 cm tall to top of inflorescences.
*Form*.—Basal clump, with about 24 stems from the base.
*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 14 inflorescences per stem.

*Size*.—To 51 cm tall to a terminal inflorescence to 10 mm wide at base.

*Strength*.—Excellent.

*Internode length*.—5 to 12 cm.

*Surface texture*.—Strigose.

*Rugosity*.—Absent.

*Variegation*.—Absent.

*Color*.—Yellow Green 147B in shade, tinted 187A in sun.

Leaf (stem):

*Type*.—Simple.

*Shape*.—Lanceolate.

*Arrangement*.—Alternate.

*Blade size*.—Grows to 11 cm long and 3.4 cm wide.

*Margins*.—Mostly entire.

*Apex*.—Acuminate.

*Base*.—Attenuate.

*Surface texture*.—Strigose on both sides.

*Venation*.—Pinnate, Yellow Green 145B on both sides.

*Color*.—Topside Green 137A, bottom side closest to Green N137A.

*Petiole description*.—Clasping, grows to 5 cm long and 4 mm wide, scabrous, narrow leafy edges, topside Yellow Green 148D lightly tinted Greyed Purple N187C , bottom side Yellow Green 145A.

Inflorescence:

*Type*.—Composite on terminal stalked heads.

*Flowering stem*.—Grows to 51 cm tall from the base of the plant to the terminal inflorescence; unbranched to branched, with 1 to 14 inflorescences per stem.

*Size*.—Grows to 8 cm wide and 5.5 cm deep as disc enlarges.

*Form*.—Ray florets held slightly down, reflexing more in very old inflorescences, mature disc is conic.

*Immature inflorescence* (*bud*).—2.7 cm wide and 1.5 cm deep, ray florets held upright at a 70 degrees angle from vertical and rolled up so only the back color shows, Red Purple 61C except tip Greyed Yellow 160C, disc color Yellow Green 147A.

*Ray florets*.—Without pistil or stamen, number about 13, full size florets grow to 42 mm long and 13 mm wide, oblanceolate with the tip usually two-or-three toothed (each acute), entire margins, base attenuate, glabrous on both sides; newly fully open florets topside closest to Red Purple 61B, bottom side Greyed Purple 186B; florets darken to topside Red Purple 60B, bottom side Red Purple 59C; fading when old.

*Disc*.—Flat becoming conic, becoming to 45 mm deep and 52 mm wide with maturity, overall color Red Purple 60B.

*Disc florets*.—To about 279 in number, each with 1 pistil and 4 stamen, grow to 22 mm long and 7 mm wide, each with one persistent bract (16 mm long with the top 4 mm colored Greyed Purple 187C on tip to 2 mm Yellow Green 147D blending to White NN155BC); showy 4 to 5 lobed corollas to 15 mm long and 6 mm wide, tubular on the bottom with the lobes spread out like a fan, glabrous on both sides, back side color Red Purple 60B on lobes lightening to White NN155B at base, inside color Red Purple 59C on lobes lighten to 63C at base; pistil 9 mm long, ovary 4 mm long, White NN155A, style 5 mm long White NN155A, 2-branched stigma spreading 1.5 mm wide, Greyed Purple 187A; stamen 5 mm long, anthers 2.7 mm long and Greyed Purple N187A, filaments 2.5 mm long, White 155A, pollen none.

*Involucral bracts*.—In 4 leafy series, area grows to 30 mm wide and 10 mm deep, lobes lanceolate in shape, reflexed, grow to 13 mm long and 3 mm wide, Green 137B, margins strigose, tip acute, strigose on both sides.

*Receptacle*.—Grows to 15 mm wide and 16 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: None.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

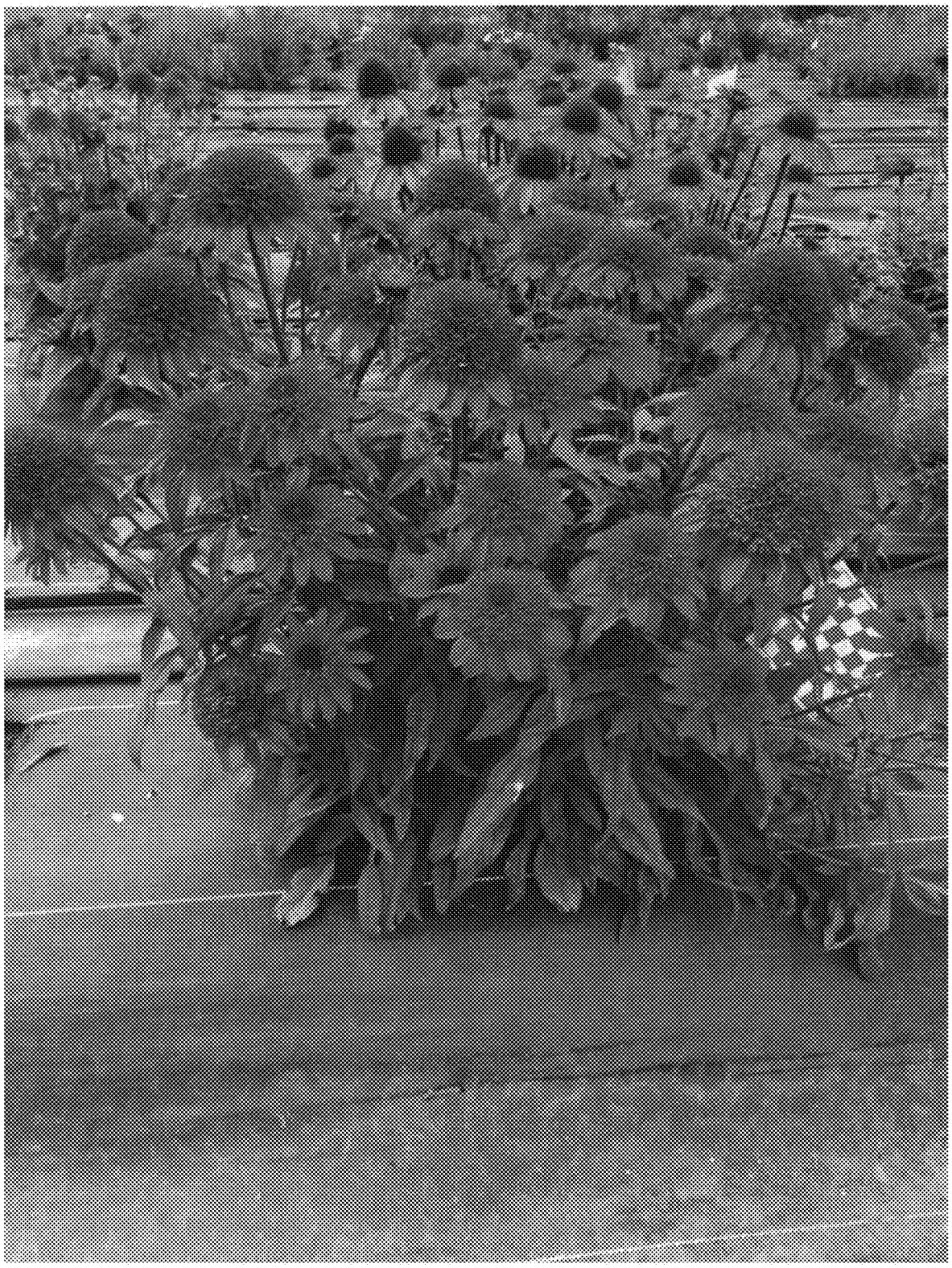

* * * * *